United States Patent [19]
Williams et al.

[11] Patent Number: 4,932,044
[45] Date of Patent: Jun. 5, 1990

[54] TISSUE ANALYZER

[75] Inventors: Robert W. Williams; Pasko Rakic, both of Hamden, Conn.

[73] Assignee: Yale University, New Haven, Conn.

[21] Appl. No.: 267,222

[22] Filed: Nov. 4, 1988

[51] Int. Cl.[5] .................... G01N 33/48; G06M 11/02; H04N 7/18

[52] U.S. Cl. ....................................... 377/10; 350/530; 382/6; 377/112

[58] Field of Search .................. 377/10, 112; 350/507, 350/529, 530; 382/6

[56] References Cited

U.S. PATENT DOCUMENTS

| | | | |
|---|---|---|---|
| 3,721,759 | 3/1973 | Lang | 350/530 |
| 4,176,376 | 11/1979 | Kamachi et al. | 377/10 |
| 4,667,335 | 5/1987 | Deindoerfer | 377/10 |

OTHER PUBLICATIONS

Frost, Harold, M.D., Henry Ford Hospital Bulletin, 8, "Measurement of Osteocytes Per Unit Volume and Volume Components of Osteocytes and Canaliculae in Man"—pp. 208-211, before 11-4-88.
Abercrombie, M., Anat. Rec. 94, 1946, "Estimation of Nuclear Population from Microtome Sections"—pp. 239-246.
Petran, M. et al, Journal of the Optical Society of America, vol. 58, No. 5, May 1968, "Tandem-Scanning Reflected-Light Microscope"—pp. 661-664.
Padawer, J., Journal of The Royal Microscopic Society, vol. 88, Pt. 3, Jun. 1968, "The Nomarski interference-contrast microscope, An experimental basis for image interpretation"—pp. 305-349.
Underwood, E. E., Journal of Microscopy, vol. 89, Pt. 2, Apr. 1969, "Stereology, or the quantitative evalutaion of microstructures"—pp. 161-180.
Glaser, Edmund M., Journal of Neuroscience Methods, 5(1982), "Snell's Law: The Bane of Computer Microscopists"—pp. 201-202.
Gunderson et al, Journal of Microscopy, vol. 131, Pt. 1, Jul. 1983, "Estimation of Section Thickness Unbiased by Cutting-Deformation"—pp. RP3-RP4.
Howard et al, Journal of Microscopy, vol. 138, Pt. 2, May 1985, "Unbiased estimation of particle density in the tandem scanning reflected light microscope"—pp. 203-212.
Curcio et al, Anat. Rec., 1986, "Computer-Assisted Morphometry Using Video-Mixed Microscopic Images and Computer Graphics"—pp. 329-337.
Gunderson, H. J. G., Journal of Microscopy, vol. 143, Pt. 1, Jul. 1986, "Stereology of arbitrary particles"—pp. 3-45.

*Primary Examiner*—John S. Heyman
*Attorney, Agent, or Firm*—Perman & Green

[57] ABSTRACT

A system is disclosed for counting particles/cells within a counting box of precisely known volume that is completely inside a transparent section or sample. The box has a chosen height with defined upper and lower limits and appropriately selected width and depth dimensions. It resides completely within the sample and has no surface in common with an exterior surface of the sample. The system includes a compound light microscope that has a depth of focus which is small in relation to the thickness dimension of the counting box. The microscope includes adjustment means for moving the focal plane through a range which is greater than the height of the counting box. Display means are provided which show the portion of the sample that is within the depth of focus and user-operated means is provided to enable the user to mark the cells so displayed. Indicator means are further provided to either audibly or visually indicate to the user when the adjustment means cause the focal plane to pass beyond either the upper or lower height limits of the counting box. The indicator means further includes means for accumulating a count of cells within the counting volume as the user operates the marker means. Means are also provided to compensate for optical foreshortening.

7 Claims, 5 Drawing Sheets

52
54
VIDEO PROCESSOR
60
62
VIDEO MIXER
66
50
56
64
MICROCOMPUTER
58
70
72
76
78
80
Z-AXIS COMPARATOR
73
68

VIDEO PROCESSOR
VIDEO MIXER
MICROCOMPUTER
Z-AXIS COMPARATOR
50
52
54
56
58
60
62
64
66
68
70
72
73
76
78
80

TISSUE ANALYZER

This invention was made with Government support under Grant numbers ROEY 02593 and PONS 22807 awarded by the Department of Health and Human Services. The Government has certain rights in the invention.

FIELD OF THE INVENTION

This invention relates to tissue analysis and, more particularly, to an apparatus for accurately counting the number of cells or particles in a section or sample of tissue.

BACKGROUND OF THE INVENTION

It is well known to scientists and physicians that the number and size of cells in a tissue sample is an important factor in determining whether tissue is healthy or diseased. For instance, the number of cells in parts of the brain is a fundamental determinant of behavior and cognitive ability. Even a small deficit or surplus in the number of neurons will have long-lasting effects on performance (e.g., Parkinson's disease, Huntington's chorea and perhaps even schizophrenia).

In the prior art there are numerous suggestions of how to count cells or particles in samples of tissue. One of the more widely used methods was described by Abercrombie in a paper entitled "Estimation of Nuclear Populations From Microtome Sections", Anat. Rec., Vol. 94, pp 239–247 (1946). Using Abercrombie's method, sections of tissue are typically cut in thicknesses of 5 to 20 microns. A counting frame is placed in the eyepiece of a conventional compound microscope and cells in each section are then counted at a magnification of 500 or higher. All cells, cell nuclei or nucleoli that are inside the frame are counted. In addition, those cells that cross 2 out of 4 edges of the four-sided frame—by convention, the right and upper edges—are also counted. In contrast, cells that cross any part of the bottom or left edges of the frame are not counted. The procedure is repeated from the top to the bottom of the section until all cells at all depths have been counted. However, during this procedure no account is actually taken of the three dimensional position of cells, and no attempt is made to determine the number of cells at the top and bottom surfaces of the section that were split or dislodged by the knife during cutting.

A more accurate counting method was described by Howard et al in a paper entitled "Unbiased Estimation Of Particle Density In The Tandem Scanning Reflected Light Microscope", Journal of Microscopy, Vol. 138, Part II, May, 1985, pp 203–212 (1985). Howard et al. suggest the direct optical examination of a cube of tissue. They point out that the sample cube is not physically sectioned but rather that it is examined in an intact state. A particular cube is chosen and the particles or cells that lie entirely inside the cube and half of those which transect its surfaces are counted.

In specific, Howard et al. studied unsectioned semi-opaque materials (entire bones) that could not be examined with a normal compound light microscope. Therefore, Howard et al were constrained to use a tandem scanning reflected light microscope (TSRLM), an expensive special-purpose microscope that accepts only directly reflected light. Such an instrument is not designed for use with conventional sectioned tissue. For a description of the TSRLM, see "Tandem-Scanning Reflected Light Microscope" by Petran et al, Journal of the Optical Society of America, Vol. 58, No. 5, May, 1968, pp 661–664.

The method of Howard et al. suffers from several additional drawbacks. It does not take into account the fact that the number of particles or cells can actually change during the preparation of a tissue sample. For instance, if the sample is prepared by microtome cutting, cells/particles can either be sectioned, pushed deeper into the sample, or pulled out of the sample. These effects are illustrated in FIG. 1 by cell 10, cell 12 and pit 14, respectively. If any cube used as suggested by Howard et al. includes such a section of tissue with altered cells, an erroneous count may occur.

In addition, the method of Howard et al. lacks a convenient way to define the cubic counting box. The upper and lower surfaces of the counting box are defined by reference to the microscope's fine-focus scale. The operator must therefore examine the fine-focus control after each movement to see whether the limits of the counting box (cube) have been reached. Thus, after each examination, the operator must glance at the picture, make the particle count and move the focus control, reexamine the position, and repeat the process iteratively until the entire depth dimension of the cube has been traversed.

Accordingly, it is an object of this invention to adapt a modified Howard et al. method to use with a conventional compound light microscope and for examination of typical sectioned materials used in histology, pathology and research.

It is still another object of this invention to facilitate the operator's definition of a counting box so that the method is easier to implement.

It is a further object of this invention to provide an improved apparatus for counting cells in a sample, which avoids inaccuracies introduced by sample preparation.

SUMMARY OF THE INVENTION

A system is disclosed for counting particles or cells within a box of precisely known volume that is completely inside a transparent section or sample. The box has a chosen height, with defined upper and lower limits and appropriately selected width dimensions. The box resides completely within the sample and has no surface in common with an exterior surface of the sample. The system includes a compound light microscope that has a depth of focus which is small in relation to the thickness dimension of the counting box. The microscope includes adjustment means for moving the focal plane through a range which is greater than the height of the counting box. Display means are provided which show the portion of the sample which is within the depth of focus. User-operated means are provided to enable the user to mark the cells so displayed. Indicator means are provided to either audibly or visually indicate to the user when the adjustment means cause the focal plane to pass beyond either the upper or lower height limits of the counting box. The indicator means further includes means for accumulating a count of cells within the counting volume as the user operates the marker means. Means are also provided to compensate for optical foreshortening.

DETAILED DESCRIPTION OF THE INVENTION

Figure 1:
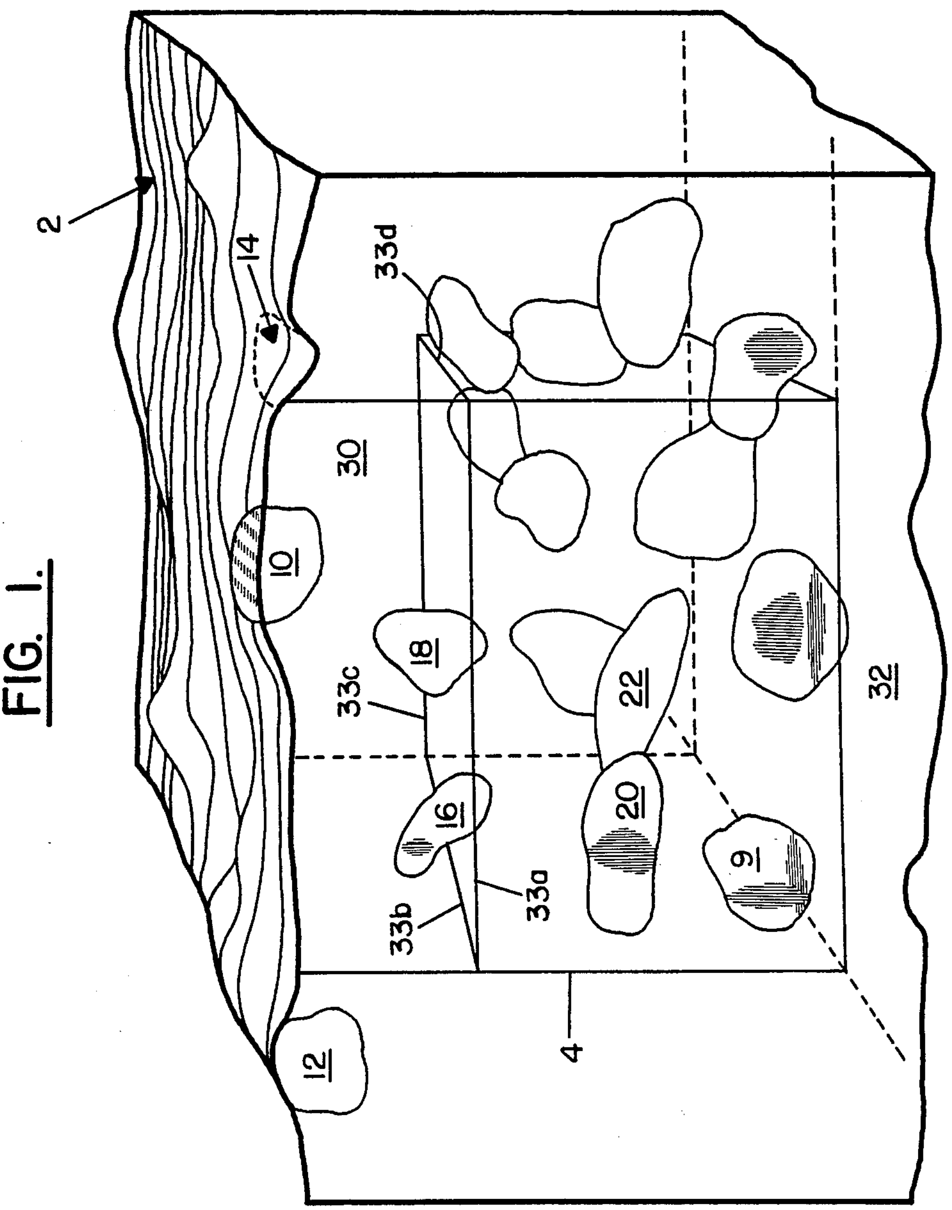
FIG. 1 is a magnified section of tissue showing a counting box in a tissue sample.

Referring now to FIG. 1, a section of tissue 2 is shown which has been greatly magnified. Tissue section 2 contains a number of cells that are to be counted. It is well known that tissue sections vary in thickness; (e.g., the thickness of a single section can vary by plus or minus 10 microns). This variation has serious detrimental affects on the accuracy of an estimate of cell number when conventional methods are used. The reason is that sample volume will vary in proportion to the variation in section thickness. This gives rise to very high sampling variations and error. This error is eliminated in this invention by selecting a counting box 4, no surface of which is coextensive with an outer surface of the tissue section. Within counting box 4, a number of cells 16, 18, 20, 22, etc., are found. In accordance with the method of Howard et al., only those cells that transect three surfaces of counting box 4 are counted, whereas those that transect the other three surfaces are ignored. For instance, cells transecting surfaces that are bounded by a dotted line in FIG. 1 would be ignored, while cells that transect surfaces bounded solely by solid lines would be counted.

Above and below counting box 4 are buffer zones 30 and 32, which should, ideally, be at least as high as the tallest cell/particle to be counted. Buffer zones 30 and 32 isolate counting box 4 from surface artifacts of all sorts.

Figure 2:
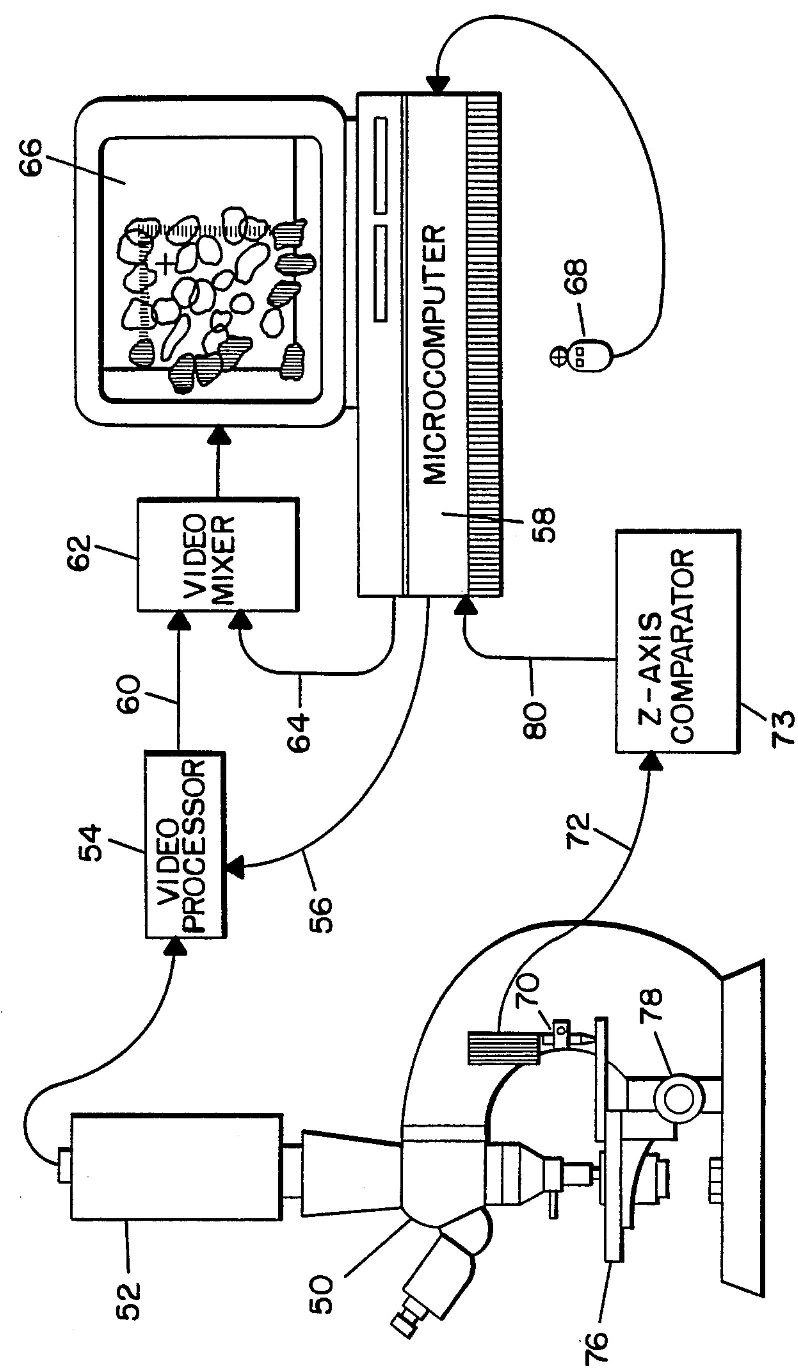
FIG. 2 is a diagram that illustrates the major components of the invention.

Referring to FIG. 2, the major components that comprise the invention will be described. Microscope 50 is a conventional compound light microscope. It is preferably provided with a high-power objective having a narrow depth of field. As will be described below, microscope 50 is further preferably provided with differential interference contrast (DIC) optics to enhance the user's ability to identify particular cell structures.

A video camera 52 is affixed, in the normal manner, to the upper portion of microscope 50 and feeds its signal to video processor 54. Video processor 54 is provided with a synchronizing input 56 from a microcomputer 58. Video processor 54 has controls that enable the operator to adjust and optimize brightness, contrast, and resolution of the image. The output signal from video processor 54 is fed via line 60 to a video mixer 62. Another input to video mixer 62 is provided via line 64 from microcomputer 58. Inputs on line 64 enable the line segments of a counting frame to be superimposed on the scene being transmitted from video processor 54. The counting frame is defined by lines 33a, 33b, 33c and 33d in FIG. 1.

The output of video mixer 62 is applied to and viewed on a video monitor 66, which preferably has the ability to provide color images to the viewer. Monitor 66 is of the "RGB" type, which enables its color presentation to be automatically controlled by signals from microcomputer 58 (i.e., its red, blue and green controls are available for individualized control). An input device 68 (e.g., mouse, keyboard) is connected to microcomputer 58 and provides the operator with the ability to construct the counting frame as well as to mark and count the cells shown on monitor 66.

As will be hereinafter understood, it is important that the height of the counting box and sample be measured with accuracy. However, it is known that the apparent height of objects examined with a microscope is a function of differences in the refractive index of the tissue, the objective, and the materials in which the tissue and slide are immersed. If a dry objective is used to focus first on the top and then on the bottom of an object, the distance the stage actually travels will only be 66% of the true distance between top and bottom. The difference is accounted for by the ratio of the refractive indices of air and crown glass (1.000:1.524). An object 45 microns high will be imaged over a vertical distance of only 30 microns. Obviously, therefore, the refraction of light is a problem when the operator tries to define the height of a counting box. Z axis comparator 73 can compensate for optical foreshortening. The operator can readily enter a correction factor that can be applied automatically.

Another solution is to use an oil immersion objective. With homogeneous oil immersion, the tissue, the materials in which the tissue is placed, and the glass of the objective have refractive indices close to each other. Immersion oil has a refractive index of 1.515. The mounting material (e.g., Fisher's Permount) has a refractive index of 1.515 (wet) or 1.529 (dry). Cellulose nitrate embedding material has a refractive index of 1.514. Cover glass has a refractive index between 1.513 and 1.534. These indices are so close to each other that the optical and the true height of an object correspond almost exactly.

Microscope 50 is preferably modified in several ways. First, it is provided with a digital micrometer 70, which provides outputs on line 72 to Z axis comparator 73 indicative of the movements of the stage 76. The position of the focal plane of microscope 50 is indicated by such outputs. Z axis comparator 73 is provided with manual inputs (not shown) which enable set points to be entered indicating the upper and lower height thresholds of the counting box. Those set points may also be entered from microcomputer 58 via line 80.

As is well known, the relative position of stage 76 may be varied by an operator's movement of the fine focus control 78. It should be understood that other position sensing devices may be used in lieu of digital micrometer 70. For instance, a shaft encoder can be attached to the fine focus control 78 to provide an input to Z axis comparator 73. However, a digital micrometer that directly senses movements of the stage is preferable because the measurements are direct. One micrometer which has been employed is the Metro-25 Digital Length Gauge, which has a range of movement of 25 millimeters, a resolution of 0.1 microns, and an accuracy of better than 0.5 microns over its full range. That micrometer was obtained from Heidenham Corporation, Elk Grove Village, Ill.

Figure 3:
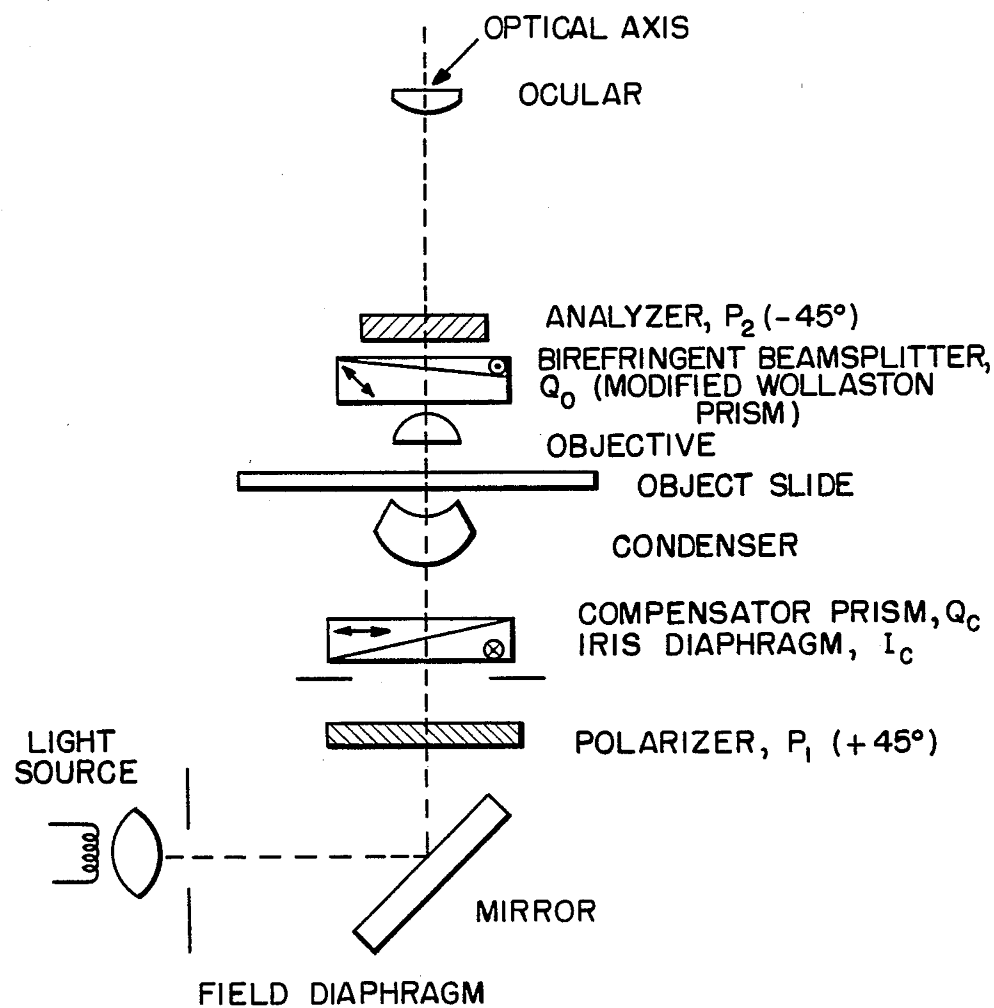
FIG. 3 is a schematic view of the major optical components of a differential interference contrast (DIC) optics system.

A second modification to the microscope involves the inclusion therein of differential interference contrast (DIC) optics. Such optics are also known as Nomarski interference-contrast optics, and this system is described by Padawer in his paper entitled "The Nomarski Interference-Contrast Microscope, An Experimental Basis for Image Interpretation," Journal of The Royal Microscope Society, Vol. 88, Part 3, June 1968 pp. 305–349. FIG. 3 shows a schematic of the optics contained in a DIC optical system.

The reason for inclusion of DIC optics is that it is often difficult to obtain high-contrast images with conventional microscope optics. The reason is that the image is partly obscured by the blur of structures just outside the microscope's plane of focus. DIC optics remove low-spatial-frequency blur while enhancing high-spatial-frequency detail. Furthermore, they tend to enhance the definition of the equatorial portion o a cell's outline (widest diameter portion of the cell). DIC images are therefore easier to focus and the operator finds it easier to decide whether the edge of a cell or particle extends beyond the boundaries of a counting box.

The DIC optical system shown in FIG. 3 may be characterized as a polarized-light interferometer. The light source is incoherent. The light traverses polarizer P1 before entering a compensator prism Qc. Polarizer P1 selects a set of light waves vibrating at +45 degrees. The light polarized at +45 degrees enters a modified Wollaston prism or birefringent beamsplitter Qo which gives rise to two orthogonally polarized wave fronts. These emerging waves are offset by a variable amount as they pass through the tissue. When these two wave fronts are brought back to the same plane above the objective, they interfere with each other. The interference between them is rendered observable when they pass through analyzer P2. This interference phenomenon substantially enhances the outlines of cells and/or particles for the microscope operator.

Figure 4A:
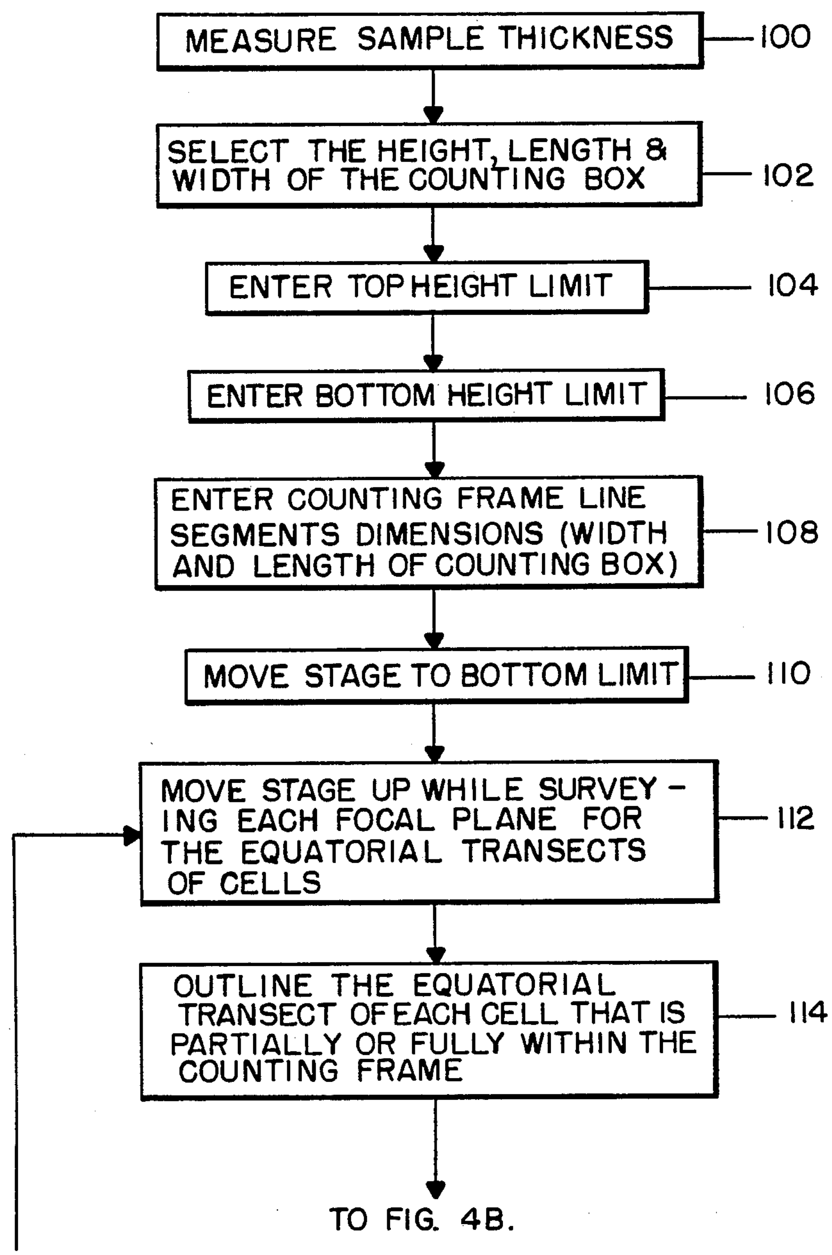
FIGS. 4a and 4b illustrate a flow diagram showing the procedure used by the invention.
Figure 4B:
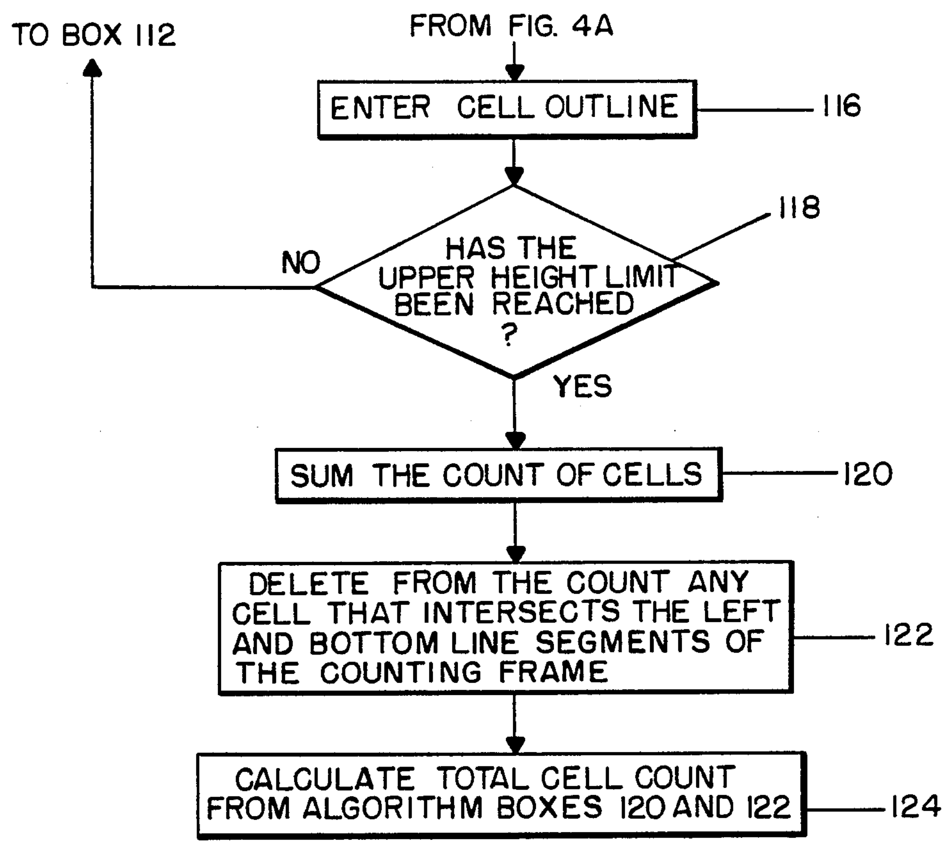

The operation of the system shown in FIG. 2 will be understood-by reference to FIGS. 4*a* and 4*b*. As shown in box 100 of FIG. 4*a*, the operator initially measures the thickness of the sample section. This is done by initially focusing on the uppermost surface of the sample and then racking down the objective until the lowermost surface is in focus. If Z axis comparator 73 (FIG. 2) is zeroed at the uppermost surface, it will indicate the thickness of the sample when the lowermost portion is in focus.

Knowing the thickness of the sample section, the operator selects the position and dimensions of the counting box (box 102). If the sample section is approximately 40 microns thick, the lower surface of the counting volume will be set approximately 3 microns above the bottom of the section and the upper surface approximately 28 microns above the bottom of the section. This gives a counting box 25 microns high. In a similar fashion, the operator chooses the length and the width of the counting frame (equivalent to the length and width of the counting box).

Subsequently, the operator enters into microcomputer 58 the top height limit of the counting box (box 104), the bottom height limit of the counting box (box 106), and the coordinates of the line segments that define the length and width of the counting frame (box 108). The operator enters the top and bottom height limits by inputting them through the keyboard of microcomputer 58. The operator enters the counting box line segments by using mouse 68 or another appropriate input device to draw orthogonal lines on display 66 and those lines define the desired length and width dimensions of the counting frame for microcomputer 58.

When the upper and lower height limits are entered into microcomputer 58, they are fed via conductor 80 (FIG. 2) to Z axis comparator 73. When it receives a signal via conductor 72 that stage 76 has reached a top or bottom height limit, Z axis comparator provides two types of outputs, each selectable by an operator. The first selectable output is an audible. alarm. that a height limit has been reached. It is preferred that the audible alarm have two distinct tones, one for the top height limit and one for the bottom limit. This enables the operator to easily distinguish, by ear, that the stage has reached an operating limit, without the need to constantly monitor the height readout.

The second type of selectable output from Z axis comparator 73 is a change in the color display on monitor 66 when a height limit has been reached. This output is sent via conductor 80 to microcomputer 58, which then inhibits a color input to monitor 66. Thus, as the operator moves stage 76, the color displayed on monitor 66 changes, thereby indicating when a top or bottom height limit of the counting box has been reached or exceeded. Preferably, one component color (e.g. red) is inhibited when passing through the bottom height limit. and a different color (e.g., blue) is inhibited when passing through the top height limit. The audible alarms and color indications may be used either separately or together.

Returning to FIG. 4*a*, the operator moves stage 76 to the bottom limit of the counting box (box 110) and then begins moving the stage upward. The operator marks and counts each cell as it comes into focus on monitor 66. The operator then uses input device 68 (box 114) to trace the outline of each in-focus cell that is partially or completely within the counting frame. In addition to keeping track of the cell tracings, microcomputer 58 keeps a count of the number of tracings (box 116). It should be remembered that cells that intersect the bottom limit are not counted. For that reason, any cell that intersects the bottom height limit is not traced or counted. These uncounted cells are recognized and rejected by commencing the stage movement below but near the bottom limit. Cells that are visible on both sides of the bottom limit are rejected.

If the upper limit of the counting box has not been reached, the procedure continues: the operator again moves the stage upward until additional cells are in focus, and then marks and then marks and counts them (decision box 118). Once the upper height limit of the counting volume is reached (as indicated to the operator by an audible alarm and/or a color change on monitor 66), the procedure branches. The operator instructs microcomputer 58 to count all cell tracings within the counting box that do not intersect a counting frame line segment (box 120). Thus, all cells whose margins lie entirely within the counting frame are counted in a cumulative manner and the value is stored. Next, the operator instructs microcomputer 58 to subtract from the count all cell tracings that intersect the line segments that define the right and top edges of the counting frame. (Cells that intersect the left and bottom edges of the counting frame are included in the count.) Microcomputer 58 accomplishes this by determining whether any solutions of the line equation for a particular counting-frame line segment lie within the limits of a cell tracing. If such an overlap is found, then it is known that the cell tracing intersects a frame line segment and is to be handled accordingly. Finally, all cells or particles whose margins lie completely inside the counting box and all cells or particles which intersect three of the six surfaces of the counting box are added to provide a complete cell count (box 124).

This process is repeated at different locations within the tissue sample and the results are combined. Subsequently, the operator can obtain an estimate of the total number of cells or particles in the tissue sample by multiplying the mean density by the total volume of the region in which the counting boxes have been located.

It should be understood that the foregoing description is only illustrative of the invention. Various alternatives and modifications can be devised by those skilled in the art without departing from the invention. Accordingly, the present invention is intended to embrace all such alternatives, modifications, and variances which fall within the scope of the appended claims.

I claim:

1. In a system for counting particles within an interior volume of a transparent sample, said volume having chosen thickness and width dimensions, said thickness dimension exhibiting upper and lower height limits, said interior volume containing no surface coincident with an exterior surface of said sample, the combination comprising:

a compound light microscope with a focal plane whose depth of field is small in relation to said thickness dimension, said microscope having adjustment means for moving said sample through a range greater than said thickness dimension;

display means for showing particles in said sample which are within said focal plane;

marker means for a marking a particle to be counted;

indicator means for indicating when said adjustment means causes said focal plane to overlap an upper or lower height limit; and means for accumulating a count of marked particles.

2. The system as recite din claim 1 wherein said compound light microscope is provided with differential interference contrast optics to enhance the particles which are within said focal plane.

3. The system of claim 1 further comprising:

means for altering the showing of said display means when said adjustment means is operated to cause said focal plane to overlap an upper or lower height limit.

4. The system of claim 3 wherein said altering means modifies said display means in a first fashion when said overlap of said upper height limit occurs and modifies said display means in a second fashion when said overlap of said lower limit occurs.

5. The system of claim 4 wherein said first fashion causes said display means to exhibit a first color and said second fashion a second color.

6. The system of claim 1 wherein said indicator means comprises alarm means which provides audible tones when said adjustment means is operated so as to cause said focal plane to overlap an upper or lower height limit.

7. The system of claim 6 wherein said alarm means provides a first audible tone when said overlap of said upper limit occurs and a different audible tone when said overlap of said lower limit occurs.

* * * * *